(12) United States Patent
Ichikawa et al.

(10) Patent No.: US 8,946,375 B2
(45) Date of Patent: Feb. 3, 2015

(54) METHOD FOR MAKING OVER-INDEXED THERMOPLASTIC POLYURETHANE ELASTOMER PRECURSOR AND THERMOPLASTIC POLYURETHANE ELASTOMER MADE FROM THE PRECURSOR

(71) Applicant: NIKE, Inc., Beaverton, OR (US)

(72) Inventors: Yasushi Ichikawa, Tualatin, OR (US); Thomas J. Kennedy, III, Wilbraham, MA (US); Chien-Hsin Chou, Yun-lin Hsien (TW); Hui-Kai Liao, Yun-lin Hsien (TW)

(73) Assignee: NIKE, Inc., Beaverton, OR (US)

( * ) Notice: Subject to any disclaimer, the term of this patent is extended or adjusted under 35 U.S.C. 154(b) by 76 days.

(21) Appl. No.: 13/730,215

(22) Filed: Dec. 28, 2012

(65) Prior Publication Data

US 2013/0211034 A1    Aug. 15, 2013

Related U.S. Application Data

(60) Provisional application No. 61/582,658, filed on Jan. 3, 2012.

(51) Int. Cl.
*C08G 18/10* (2006.01)
*C08G 18/28* (2006.01)
(Continued)

(52) U.S. Cl.
CPC .............. *C08G 18/28* (2013.01); *C07C 263/16* (2013.01); *C08G 18/4854* (2013.01); *C08G 18/6674* (2013.01); *C08G 18/675* (2013.01); *C08G 18/7671* (2013.01); *C08G 18/86* (2013.01); *C08G 18/12* (2013.01); *C09D 175/04* (2013.01); *A63B 37/0024* (2013.01); *A63B 37/0027* (2013.01); *A63B 37/0039* (2013.01);
(Continued)

(58) Field of Classification Search
USPC ........ 528/65, 66, 76, 85; 264/177.17–177.19, 264/211.12, 211.13, 211.18, 211.2, 264/211.23–211.24, 311.11, 331.19
See application file for complete search history.

(56) References Cited

U.S. PATENT DOCUMENTS

| 4,293,679 A | 10/1981 | Cogliano |
| 2004/0157945 A1 | 8/2004 | Barber |

(Continued)

FOREIGN PATENT DOCUMENTS

| EP | 0632077 A2 | 1/1995 |
| KR | 10-1047087 B1 | 7/2011 |

OTHER PUBLICATIONS

Notification of Transmittal of the International Search Report and the Written Opinion of the International Searching Authority mailed on May 29, 2013 in connection with International Patent Application Serial No. PCT/US2013/020083; 14 pages.

(Continued)

*Primary Examiner* — Michael L Leonard
(74) *Attorney, Agent, or Firm* — Honigman Miller Schwartz and Cohn LLP; Anna M. Budde; Jonathan P. O'Brien (57) ABSTRACT

A method for making over-indexed thermoplastic polyurethane elastomer precursor. The precursor may be crosslinked.

31 Claims, 2 Drawing Sheets

(51) Int. Cl.
*C07C 263/16* (2006.01)
*C08G 18/48* (2006.01)
*C08G 18/66* (2006.01)
*C08G 18/67* (2006.01)
*C08G 18/76* (2006.01)
*C08G 18/86* (2006.01)
*C08G 18/12* (2006.01)
*C09D 175/04* (2006.01)
*A63B 37/00* (2006.01)
*B29L 31/54* (2006.01)
*B29C 45/00* (2006.01)

(52) U.S. Cl.
CPC ......... *A63B37/0051* (2013.01); *A63B 37/0058* (2013.01); *B29L 2031/546* (2013.01); *B29C 45/0001* (2013.01)
USPC .................. 528/85; 528/65; 528/66; 528/76; 264/177.17; 264/177.18; 264/177.19; 264/211.12; 264/211.13; 264/211.18; 264/211.2; 264/211.23; 264/211.24; 264/331.19

(56) References Cited

U.S. PATENT DOCUMENTS

| | | |
|---|---|---|
| 2004/0219995 A1 | 11/2004 | Sullivan |
| 2008/0274827 A1 | 11/2008 | Matroni et al. |
| 2009/0028975 A1* | 1/2009 | Eloo ............................. 425/68 |
| 2009/0198036 A1* | 8/2009 | Duffy ............................. 528/85 |
| 2010/0331113 A1 | 12/2010 | Shiga et al. |
| 2011/0064883 A1 | 3/2011 | Goodwin |
| 2011/0081492 A1 | 4/2011 | Michalewich et al. |
| 2012/0004052 A1* | 1/2012 | Chou et al. ................... 473/376 |
| 2012/0225738 A1 | 9/2012 | Ishii et al. |

OTHER PUBLICATIONS

Notification of Transmittal of the International Search Report and the Written Opinion of the International Searching Authority mailed on May 29, 2013 in connection with International Patent Application Serial No. PCT/US2013/020078; 14 pages.

Notification of Transmittal of the International Search Report and the Written Opinion of the International Searching Authority mailed on May 13, 2013 in connection with International Patent Application Serial No. PCT/US2013/020013; 12 pages.

* cited by examiner

METHOD FOR MAKING OVER-INDEXED THERMOPLASTIC POLYURETHANE ELASTOMER PRECURSOR AND THERMOPLASTIC POLYURETHANE ELASTOMER MADE FROM THE PRECURSOR

This application claims priority under 35 U.S.C. §119(e) to U.S. Provisional Patent Application No. 61/582,658, entitled METHOD FOR MAKING OVER-INDEXED THERMOPLASTIC POLYURETHANE ELASTOMER PRECURSOR AND THERMOPLASTIC POLYURETHANE ELASTOMER MADE FROM THE PRECURSOR, and filed Jan. 3, 2012, which application is hereby incorporated by reference.

BACKGROUND OF THE INVENTION

1. Field of the Invention

The present invention relates to a method for making over-indexed thermoplastic polyurethane elastomer precursor. The invention also relates to thermoplastic polyurethane elastomer made from the precursor.

2. Description of Related Art

Polyurethane is a polymer widely used in many industries. One feature of polyurethane is that it can be made in thermoplastic form or thermoset form. Thermoplastic polymer materials may be reversibly melted, and so may be used in a variety of manufacturing techniques, such as compression molding, that take advantage of this property. On the other hand, thermoset polymer materials are generally formed by mixing two or more components to form a cured polymer material that cannot be re-melted or re-worked. Each type of polymer material present advantages and disadvantages when used to manufacture various articles, including golf balls.

Because polyurethane typically is the reaction product of an isocyanate moiety and a hydroxyl moiety, the properties and characteristics of polyurethane can be adjusted to an extent by selecting specific reactants. For example, both long-chain polyols and short polyols often are used in the same polyurethane molecule. Long-chain polyols provide soft areas or segments in the polyurethane and short-chain polyols, in combination with isocyanate, form hard areas or segments in the polyurethane. However, the identity and molecular weight of reactants are not the only determinants of the properties and characteristics of the polyurethane product, as can be seen from the differences between thermoset and thermoplastic forms of polyurethane.

In golf ball technology, many attempts have been made to use thermoset polyurethane elastomers as a substitute for early (balata) and late (ionomers) compositions for making, for example, outer cover layers. Ionomers often are softened to improve feel and control. Thermoset polyurethane elastomers are relatively inexpensive and offer good hitting feel and good scuff resistance. Particularly, thermoset polyurethane elastomers may present improvements in the scuff resistance as compared to softened ionomer resin blends. However, thermoset materials require complex manufacturing processes to introduce the raw material and then effect a curing reaction, which causes the manufacturing process to be less efficient.

Although thermoset polyurethane can be made into tough, damage-resistant articles, these articles are not easily recycled. Thermoplastic polyurethane is softened by heat and therefore is amenable to recycling. Thermoplastic polyurethane often is made by preparing a precursor, and typically is cured in stages during various processing steps. However, thermoplastic polyurethane typically is less durable and less scuff-resistant than thermoset polyurethane.

Whereas it is possible to proceed in continuous processing steps from reactants (isocyanate and hydroxyl, for example) to finished product, such processing typically is difficult to carry out successfully and efficiently. Such continuous processing typically requires coordination of many different processes and often requires integration of another product, such as a product to be covered by the polyurethane, into the manufacturing processing. Such coordination is difficult. Thus, a typical operating technique is to manufacture thermoplastic polyurethane separately, and then to use this pre-made product to form the article. In this way, processing is segmented and provides easier management of each segment.

Additional challenges are introduced when the thermoplastic polyurethane is over-indexed. Manufacture and storage of over-indexed polyurethane is typical, but free isocyanate moieties in the product are known to be hygroscopic and to react in the presence of water. Therefore, current processing technique for such stored thermoplastic polyurethane requires drying before use. Even so, this process has been found wanting, and the resultant thermoplastic polyurethane elastomer may have inferior quality.

Although golf ball technology is a significant user of thermoplastic polyurethane, scuff-resistant, durable materials also are important in other technologies. For example, articles such as livestock identity tags, shoe soles, luggage tags, and sports balls of many types, require a durable, tough product, good Shore D hardness, and flexural modulus. A scuff-resistant surface also may be useful.

Accordingly, for the foregoing reasons, there is a need in the art for a system and method that addresses the shortcomings of the prior art discussed above. In particular, there exists a need for a thermoplastic polyurethane elastomer that is durable and resistant to scuffing from use.

SUMMARY OF THE INVENTION

In one aspect, this disclosure relates to a method for making a thermoplastic polyurethane elastomer precursor. The precursor is over-indexed, i.e., has a molar excess of isocyanate moieties over hydroxyl or other reactants with the isocyanate. These isocyanate moieties are available for reaction with water in the second of a two-step curing process. The resultant polyurethane/urea hybrid is an over-indexed thermoplastic polyurethane elastomer that is durable and tough, and may be resistant to scuffing.

In another aspect, the over-indexed thermoplastic polyurethane elastomer precursor also is cross-linked. The thermoplastic polyurethane elastomer precursor has hard segments and soft segments, with optional cross-links in the hard segments. The cross-links are the reaction product of unsaturated bonds pendant from the hard segments, as catalyzed by a free-radical initiator. The resultant over-indexed cross-linked thermoplastic polyurethane elastomer is tough, durable, and may be resistant to scuffing.

Another aspect of the disclosure relates to an over-indexed, cross-linked thermoplastic polyurethane elastomer precursor that is the reaction product formed from reacting (a) a stoichiometric excess of at least about 1 mol percent of organic isocyanate moieties to the hydroxyl (or oxyhydrogen) moieties of the other reactants in the reaction product with a mixture of the following reactants:

(b) an unsaturated diol, having two primary hydroxyl groups and at least one allyl ether side group, of the formula in which $R^1$ may be any substituted or unsubstituted alkyl, substituted or unsubstituted aryl, substituted or unsubstituted alkyl-aryl group, substituted or unsubstituted ether group, substituted or unsubstituted ester group, any combination of the above groups, or H, and may optionally include an unsaturated bond in any main chain or side chain of any group; $R^2$ may be any suitable substituted or unsubstituted alkyl, substituted or unsubstituted aryl, substituted or unsubstituted alkyl-aryl group, substituted or unsubstituted ether group, substituted or unsubstituted ester group, any combination of the above groups; and $R^2$ includes an allyl group; and x and y are integers independently having any value from 1 to 10;

(c) a chain extender, having at least two reaction sites with isocyanates and having a molecular weight of less than about 450;

(d) a long chain polyol having a molecular weight of between about 500 and about 4,000; and (e) a sufficient amount of free radical initiator, so as to be capable of generating free radicals that induce cross-linking structures in the hard segments by free radical initiation.

The precursor composition exhibits a dual cure phenomenon. The manufacture of the precursor composition provides a partial cure, and then the composition is moisture-cured to form a polyurethane/urea hybrid composition, which is an over-indexed, optionally cross-linked thermoplastic polyurethane elastomer disclosed herein.

Another aspect of this disclosure relates to a method by which the over-indexed, optionally cross-linked TPU elastomer precursor is made. In accordance with an embodiment of the method, the ingredients are combined in a mixing device, typically an extruder, and are allowed to react. The free radical initiator (for crosslinking) can be included in the extruder or at any subsequent processing step. The thermoplastic polyurethane elastomer precursor is extruded, then cooled, dried, and further processed in a manner that yields an over-indexed, optionally cross-linked thermoplastic polyurethane elastomer product containing a stoichiometric excess of isocyanate moieties.

Another aspect of the disclosure is directed to articles that require a tough, durable product that has a good Shore D hardness and flexural modulus, and may have a scuff-resistant surface. Such articles (golf balls, luggage tags, shoe soles), or the surfaces thereof, can be made from the over-indexed, optionally cross-linked thermoplastic polyurethane elastomer precursor of the disclosure, just as with the method of making golf balls disclosed herein.

Other systems, methods, features, and advantages of the invention will be, or will become, apparent to one of ordinary skill in the art upon examination of the following figures and detailed description. It is intended that all such additional systems, methods, features and advantages be included within this description and this summary, be within the scope of the invention, and be protected by the following claims.

BRIEF DESCRIPTION OF THE DRAWINGS

The invention can be better understood with reference to the following drawing and description. The components in the figure are not necessarily to scale, emphasis instead being placed upon illustrating the principles of the invention. Moreover, in the figure, like reference numerals designate corresponding parts throughout the different views.

DETAILED DESCRIPTION

As used herein, unless otherwise stated, compression deformation, hardness, COR, flexural modulus, and Vicat softening temperature are measured as follows:

A. Compression deformation: The compression deformation herein indicates the deformation amount of the ball, or any portion thereof, under a force; specifically, when the force is increased to become 130 kg from 10 kg, the deformation amount of the ball or portion thereof under the force of 130 kg reduced by the deformation amount of the ball or portion thereof under the force of 10 kg is the compression deformation value of the ball or portion thereof.

B. Hardness: Hardness of a golf ball layer is measured generally in accordance with ASTM D-2240, but measured on the land area of a curved surface of a molded ball.

C. Method of measuring COR: A golf ball for test is fired by an air cannon at an initial velocity of 40 m/sec, and a speed monitoring device is located over a distance of 0.6 to 0.9 meters from the cannon. The golf ball strikes a steel plate positioned about 1.2 meters away from the air cannon and rebounds through the speed-monitoring device. The return velocity divided by the initial velocity is the COR.

D. Flexural modulus: Measured in accordance with ASTM D-790.

E. Vicat softening temperature: Measured in accordance with ASTM D-1525.

F. 100% Modulus: Also known as M100—measured in accordance with ASTM D-412.

Generally, this disclosure provides an over-indexed, optionally cross-linked thermoplastic polyurethane elastomer precursor, a method of making the over-indexed, optionally cross-linked precursor, and a method of making the over-indexed, optionally cross-linked thermoplastic polyurethane elastomer.

The over-indexed, optionally cross-linked thermoplastic polyurethane composition exhibits a dual cure phenomenon. This disclosure also provides a method of making articles, particularly golf balls, from the precursor. In particular, in embodiments relating to golf balls and other articles requiring a tough, durable, or scuff-resistant surface, the outer cover layer is made from the over-indexed, optionally cross-linked thermoplastic polyurethane. As a result of the dual cure phenomenon, the toughness, durability, or scuff resistance of a golf ball's outer cover, or of the outer surface of any article, may be greatly improved. Where present, cross-links are formed in the hard segments. Thermoplastic polyurethane elastomer having these cross-links provides superior scuff resistance.

The aspects of this disclosure that relate to use of the over-indexed, optionally cross-linked thermoplastic polyurethane in a golf ball may be applied to any golf ball precursor having any number of layers or pieces. The construction of a golf ball made according to the present method is not limited to the embodiments mentioned with specificity herein. For example, a golf ball in accordance with this disclosure may generally take any construction, such as a regulation or non-regulation construction. Regulation golf balls are golf balls which meet the Rules of Golf as approved by the United States Golf Association (USGA). Co-pending U.S. patent application Ser. No. 13/342,551, filed Jan. 3, 2012, and entitled "Over-Indexed Thermoplastic Polyurethane Elastomer, Method Of Making, And Articles Comprising The Elastomer," and co-pending U.S. patent application Ser. No. 13/342,564, filed Jan. 3, 2012, and entitled "Golf Ball Having An Over-Indexed Thermoplastic Polyurethane Elastomer Cover and Having A Soft Feeling When Hit,", the entireties of which are hereby incorporated by reference, describe golf balls in which aspects of this disclosure are useful.

Figure 1:
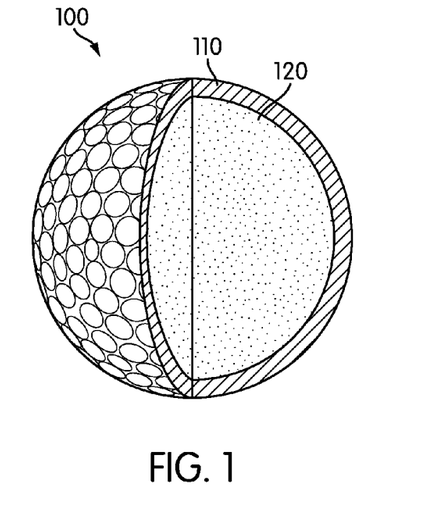
FIG. 1 shows a golf ball having aspects in accordance with this disclosure, the golf ball being of a two-piece construction.
Figure 2:
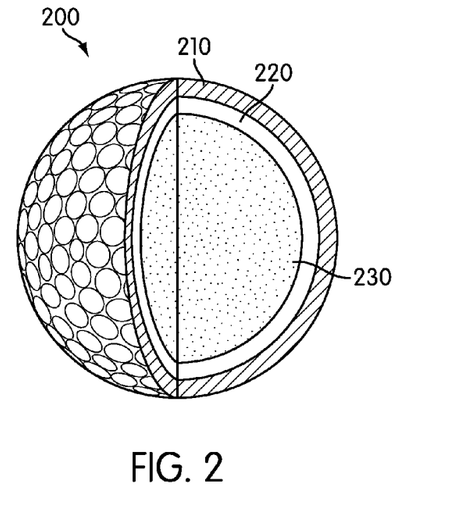
FIG. 2 shows a second golf ball having aspects in accordance with this disclosure, the second golf ball having an inner cover layer and an outer cover layer.
Figure 3:
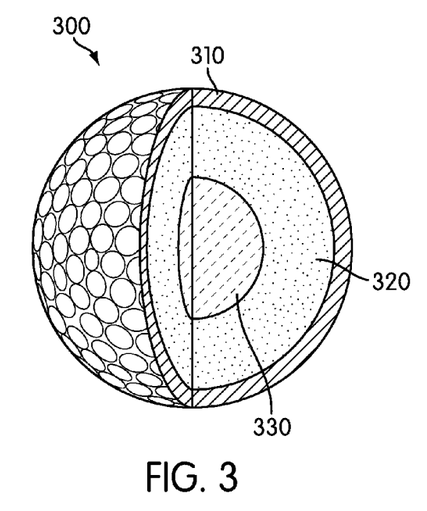
FIG. 3 shows a third golf ball having aspects in accordance with this disclosure, the third golf ball having an inner core layer and an outer core layer.
Figure 4:
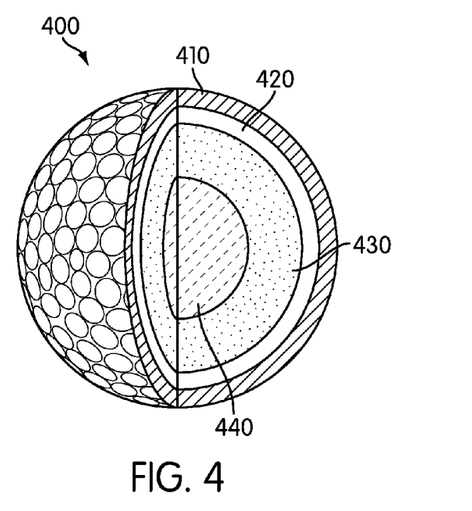
FIG. 4 shows a fourth golf ball having aspects in accordance with this disclosure, the four golf ball having an inner core layer, an outer core layer, an inner cover layer, and an outer cover layer.

Thus, the disclosure herein can be applied to any of the balls illustrated in FIGS. 1-4. For example, FIG. 1 shows a golf ball 100 having a two-piece construction comprising core 120 and cover layer 110. FIG. 2 shows a second golf ball 200 having a three-piece construction comprising core 230, inner cover layer 220, and an outer cover layer 210. FIG. 3 shows a third golf ball 300 having a three-piece construction comprising inner core layer 330, an outer core layer 320, and outer cover layer 310. FIG. 4 shows a fourth golf ball 400 having inner core layer 440, outer core layer 430, inner cover layer 420, and outer cover layer 410. Typically, each layer essentially encompasses interior layers.

The disclosure thus can be applied, not only to these golf balls, but also to golf balls having 5 or more layers, or pieces. However, for convenience herein, the disclosure will be related only to a four-piece, or four-layer, ball.

FIG. 4 shows a golf ball 400 made in accordance with the method of the present invention. Golf ball 400 includes an inner core layer 440, an outer core layer 430 substantially surrounding inner core layer 440, an inner cover layer 420 substantially surrounding outer core layer 430, and an outer cover layer 410 substantially surrounding inner cover layer 420, wherein outer cover 410 comprises the over-indexed, optionally cross-linked, thermoplastic polyurethane elastomer disclosed herein.

In some embodiments of the present invention, outer cover layer 410 may have a material Shore D hardness (measured on a slab) of from 30 to 45 and a ball surface Shore D hardness of from about 45 to about 65, typically from about 50 to about 60. Typically, the ball surface Shore D hardness is from about 55 to about 60. Outer cover layer 410 may have a flexural modulus of less than about 1,000 psi, typically less than about 800 psi. These properties and characteristics also inure to any article made from thermoplastic polyurethane elastomer precursor disclosed herein.

Both the over-indexed thermoplastic polyurethane elastomer precursor and the over-indexed cross-linked thermoplastic polyurethane elastomer precursor may include hard segments and soft segments, as thermoplastic polyurethanes are known to include. Thermoplastic polyurethanes are generally made up of (1) a long chain polyol, (2) a relatively short chain extender, and (3) a diisocyanate. Once reacted, the portions of the polymer chain made up of the chain extender and diisocyanate generally align themselves into semi-crystalline structures through weak (i.e., non-covalent) association, such as through Van der Waals forces, dipole-dipole interactions or hydrogen bonding. These portions are commonly referred to as the hard segments, because the semi-crystalline structure is harder than the amorphous portions made up of the long chain polyol.

The over-indexed cross-linked thermoplastic polyurethane elastomer precursor may include cross-links located specifically in the hard segments. These cross-links may be the reaction product of unsaturated bonds located in the hard segments, as catalyzed by a free radical initiator. These unsaturated bonds may be introduced into the hard segments by the use of unsaturated diols as chain extenders. In particular embodiments, the cross-links may be formed from allyl ether side groups present in the hard segments.

In specific embodiments, the composition of an over-indexed cross-linked thermoplastic polyurethane elastomer precursor may be derived from reacting the following:

(a) a stoichiometric excess of at least about 1 mol percent of organic isocyanate moieties to the hydroxyl (or oxyhydrogen) moieties of the other reactants in the reaction product with a mixture of the following reactants:

(b) an unsaturated diol, having two primary hydroxyl groups and at least one allyl ether side group, of the formula in which $R^1$ may be any substituted or unsubstituted alkyl, substituted or unsubstituted aryl, substituted or unsubstituted alkyl-aryl group, substituted or unsubstituted ether group, substituted or unsubstituted ester group, any combination of the above groups, or H, and may optionally include an unsaturated bond in any main chain or side chain of any group; $R^2$ may be any suitable substituted or unsubstituted alkyl, substituted or unsubstituted aryl, substituted or unsubstituted alkyl-aryl group, substituted or unsubstituted ether group, substituted or unsubstituted ester group, any combination of the above groups; and $R^2$ includes an allyl group; and x and y are integers independently having any value from 1 to 10;

(c) a chain extender, having at least two reaction sites with isocyanates and having a molecular weight of less than about 450;

(d) a long chain polyol having a molecular weight of between about 500 and about 4,000; and (e) a sufficient amount of free radical initiator, so as to be capable of generating free radicals that induce cross-linking structures in the hard segments by free radical initiation.

To form the over-indexed, optionally cross-linked thermoplastic polyurethane elastomer, the precursor disclosed herein then is treated with moisture to cure the precursor and form an over-indexed, optionally cross-linked thermoplastic polyurethane elastomer. Thus, an article can be fully cured in this way.

The above-mentioned chemical groups may have their conventional definitions as is generally known in the art of chemistry. Specifically, an unsubstituted alkyl group includes any chemical group comprising only carbon and hydrogen linked by single bonds. A substituted alkyl group may include atoms other than carbon and hydrogen in a side chain portion, such as a halogen group, an inorganic group, or other well-known functional groups. In some embodiments, a substituted or unsubstituted alkyl group may include from 1 to about 100 carbon atoms in the alkyl chain. In other embodiments, a substituted or unsubstituted alkyl group may have from 1 to 10 carbon atoms in the alkyl chain. An alkyl group, or any portion thereof, or alkyl substituent, may be a straight chain or branched.

As is further known in the art of chemistry, an aryl group is defined as any group that includes an aromatic benzene ring. Furthermore, an alkyl-aryl group includes at least one aromatic benzene ring in addition to at least one alkyl carbon. An ether group includes at least one oxygen atom bonded to two carbon atoms. An ester group includes at least one carbon atom that is double bonded to a first oxygen atom and single bonded to a second oxygen atom.

In some embodiments substituted groups, such as a substituted alkyl group or a substitute aryl group, may be substituted with another of the same group. For example, an alkyl may be substituted with another alkyl to create a branched alkyl group. In other embodiments substituted groups may be substituted with a different group, for example an alkyl may be substituted with an ether group, or an ether group may be substituted with an alkyl group. A person having ordinary skill in the art of chemistry may also synthesize suitable combinations of these groups, as may be desired.

The method of the present disclosure, and the products manufactured therefrom, include a molar ratio of the organic isocyanate moieties to the hydroxyl (or oxyhydrogen) moieties of the other reactants is at least about 1.01:1.00, typically at least about 1.06:1.00, more typically from about 1.06:1.00 to about 1.18:1.00, or from about 1.10:1.00 to about 1.15:1.00. The disclosure also contemplates embodiments in which the molar ratio is from about 1.01:1.00 to about 1.35:1.00, typically from about 1.06:1.00 to about 1.35:1.00, more typically from about 1.06:1.00 and about 1.25:1.00, and even more typically from about 1.12:1.00 to about 1.18:1.00.

The skilled practitioner recognizes that this molar ratio of isocyanate moieties to hydroxyl moieties is known as the "NCO index" or, simply, the Index. Thus, the molar ratio of 1.06:1.00 would be expressed as an index of 1.06. The terms 'index' and 'molar ratio' are used interchangeably herein.

Additional cross-linking agents also may be incorporated in the thermoplastic polyurethane elastomer precursor disclosed herein. These agents have at least 2 functional groups. Each such unsaturated functional group reacts with the unsaturated moieties in the unsaturated diol of different polyurethane molecules by free-radical or other polymerization to cross-link the molecules.

Each of the above listed reactants will be discussed in further detail, with the understanding that any particular embodiment of a specific reactant may be mixed and matched with any other specific embodiment of another reactant according to the general formulation above. Furthermore, any reactant may generally be used in combination with other reactants of the same type, such that any list herein may be assumed to include mixtures thereof, unless otherwise specified.

The organic isocyanate may include any of the known aromatic, aliphatic, and cycloaliphatic di- or poly-isocyanates. Examples of suitable isocyanates include: 2,2'-, 2,4'- (and particularly) 4,4'-diphenylmethane diisocyanate (MDI), and isomeric mixtures thereof; polyphenylene polymethylene polyisocyanates(poly-MDI, PMDI); 2,4- and 2,6-toluene diisocyanates, and isomeric mixtures thereof such as an 80:20 mixture of the 2,4- and 2,6-isomers (TDI); the saturated, isophorone diisocyanate; 1,4-diisocyanatobutane; 1,5-diisocyanatopentane; 1,6-diisocyanatohexane; 1,4-cyclohexane diisocyanate; cycloaliphatic analogs of PMDI; and the like.

Suitable chain extenders may include the common diols, such as ethylene glycol, diethylene glycol, triethylene glycol, propylene glycol, dipropylene glycol, tripropylene glycol, 1,3-propanediol, 1,4-butanediol, 1,6-hexanediol, 1,10-decanediol, neopentyl glycol, dihydroxyethoxy hydroquinone, 1,4-cyclo-hexanedimethanol, 1,4-dihydroxycyclohexane, and the like. Minor amounts of cross-linking agents such as glycerine, trimethylolpropane, diethanolamine, and triethanolamine may be used in conjunction with the diol chain extenders.

The skilled practitioner recognizes that the reaction product of isocyanate and hydroxyl moieties is a urethane. However, isocyanate also is reactive with amines, with the reaction product forming a urea. Therefore, in addition to the common diol chain extenders, diamines and amino alcohols may also be used to make over-indexed, optionally cross-linked thermoplastic polyurethane elastomer precursor. Examples of suitable diamines include aliphatic, cycloaliphatic, or aromatic diamines. In particular, a diamine chain extender may be ethylene diamine, hexamethylene diamine, 1,4-cyclohexylene diamine, benzidine, toluene diamine, diaminodiphenyl methane, the isomers of phenylene diamine or hydrazine. Aromatic amines may also be used, such as MOCA (4,4'-methylene-bis-o-chloroaniline), M-CDEA (4,4'-methylenebis(3-chloro-2,6-diethyl-aniline)). Examples of suitable amino alcohols, which can result in both urea and urethane structures, include ethanol amine, N-methylethanolamine, N-butylethanolamine, N-oleylethanolamine, N-cyclohexylisopropanolamine, and the like. Mixtures of various types of chain extenders may also be used to form the cross-linked thermoplastic polyurethane.

The long chain polyol ("the polyol") may generally be a polyester polyol or a polyether polyol. Accordingly, the over-indexed cross-linked thermoplastic polyurethane may be either general type of polyurethane: a polyether-based polyurethane elastomer precursor or a polyester-based polyurethane elastomer precursor, or mixtures thereof.

The long chain polyol may be a polyhydroxy compound having a molecular weight between 500 and 4,000. Suitable long chain polyols may generally include linear polyesters, polyethers, polycarbonates, polylactones (e.g., ε-caprolactone), and mixtures thereof. In addition to polyols having hydroxyl terminal groups, the polyol may include carboxyl, amino or mercapto terminal groups.

Polyester polyols are produced by the reaction of dicarboxylic acids and diols or an esterifiable derivative thereof. Examples of suitable dicarboxylic acids include succinic acid, glutaric acid, adipic acid, suberic acid, azelaic acid, sebacic acid, decanedicarboxylic acid, maleic acid, fumaric acid, phthalic acid, isophthalic acid, and terephthalic acid. Examples of suitable diols include ethanediol, diethylene glycol, 1,2- and 1,3-propanediol, dipropylene glycol, 1,4-butanediol, 1,5-pentanediol, 1,6-hexanediol, 1,10-decanediol, glycerine and trimethylolpropanes, tripropylene glycol, tetraethylene glycol, tetrapropylene glycol, tetramethylene glycol, 1,4-cyclohexane-dimethanol, and the like. Both of the dicarboxylic acids and diols can be used individually or in mixtures to make specific polyesters in the practice applications.

Polyether polyols are prepared by the ring-opening addition polymerization of an alkylene oxide with an initiator of a polyhydric alcohol. Examples of suitable polyether polyols are polypropylene glycol (PPG), polyethylene glycol (PEG), polytetramethylene ether glycol (PTMEG). Block copolymers such as combinations of polyoxypropylene and polyoxyethylene glycols, poly-1,2-oxybutylene and polyoxyethylene glycols, poly-1,4-tetramethylene and polyoxyethylene glycols are also preferred in the present invention.

Polycarbonate polyols are made through a condensation reaction of diols with phosgene, chloroformic acid ester, dialkyl carbonate, or diallyl carbonate. Examples of diols in the suitable polycarbonate polyols of the cross-linked thermoplastic polyurethane elastomers are ethanediol, diethylene glycol, 1,3-butanediol, 1,4-butanediol, 1,6-hexanediol, neopentylglycol, and 1,5-pentanediol.

Additional di- or multi-functional cross-linking agents also may be included in the thermoplastic polyurethane elastomer. One class of suitable compounds is diacrylates, particularly diacrylates having terminal unsaturation. One such compound is 1,6-hexanediol diacrylate, a commercially-available product. Other similar diacrylates also are suitable.

The over-indexed, optionally cross-linked thermoplastic polyurethane elastomer precursor may comprise a sufficient amount of free radical initiator so as to be capable of inducing cross-linking structures in the hard segments by free radical initiation at the unsaturated moiety. The free radical initiator may generate free radicals through thermal cleavage or UV radiation. When the half-life of the free radical initiator and its operation temperature are considered in the manufacturing process, the weight ratio of initiators to unsaturated diols may be from 100:0.1 to 100:100. In particular embodiments, the weight ratio of free radical initiator to unsaturated diols may be about 5:100.

Any of a variety of known free radical initiators may be used as the radical source in order to make the over-indexed cross-linked polyurethane elastomer having a cross-linked structure. Suitable radical initiators may include peroxides, sulfurs, and sulfides, and peroxides may be particularly suitable in some embodiments. The peroxides may be aliphatic peroxides or and aromatic peroxides, or mixtures thereof. Aromatic peroxides, such as diacetylperoxide, di-tert-butylperoxide, dicumylperoxide, dibenzoylperoxide, 2,5-dimethyl-2,5-di(benzoylperoxy)hexane, 2,5-dimethyl-2,5-di(butylperoxy)-3-hexyne, 2,5-bis-(t-butylperoxy)-2,5-dimethyl hexane, n-butyl-4,4-bis(t-butylperoxyl)valerate, 1,4-bis-(t-butylperoxyisopropyl)-benzene, t-butyl peroxybenzoate, 1,1-bis-(t-butylperoxy)-3,3,5 tri-methylcyclohexane, and di(2,4-dichloro-benzoyl) may be used as the free radical initiator in some embodiments. The skilled practitioner recognizes that the free radical initiators begin to act at different temperatures. For example, dicumyl peroxide begins initiation at a higher temperature than does benzoyl peroxide. With the guidance provided herein, the skilled practitioner will be able to select a suitable initiator.

Cross-links are introduced by an unsaturated diol for cross-linking, i.e., generally any diol having at least one unsaturated bond. As is generally known, an unsaturated bond may be a double bond between two carbon atoms (as in an alkene) or a triple bond (as in an alkyne). In particular embodiments, the unsaturated diol may have two primary alcohol groups. The presence of two primary alcohol groups may result in favorable reaction kinetics, such that the cross-linked thermoplastic polyurethane may be formed in an easily controlled "one step" continuous process.

In particular embodiments, the unsaturated diol may have two primary hydroxyl groups and at least one allyl ether side group, so as to be of the formula:

in which R is alkyl group with or without modified functional groups, and x and y are integers of 1 to 4. In particular embodiments, x and y may both have values of 1, 2, 3 or 4. In other embodiments, x and y may each have different values of between 1 and 4.

In one particular embodiment, the unsaturated diol may be trimethylolpropane monoallylether ("TMPME"). TMPME may also be named "trimethylol propane monoallyl ether", "trimethylol propane monoallylether", or "trimethylolpropane monoallyl ether." TMPME has CAS no. 682-11-1. TMPME may also be referred to as 1,3-Propanediol, 2-ethyl-2-[(2-propen-1-yloxy)methyl] or as 2-allyloxymethyl-2-ethyl-1,3-propanediol. TMPME is commercially available from Perstorp Specialty Chemicals AB.

Other suitable compounds that may be used as the unsaturated diol of formula (1) may include: 1,3-Propanediol, 2-(2-propen-1-yl)-2-[(2-propen-1-yloxy)methyl]; 1,3-Propanediol, 2-methyl-2-[(2-propen-1-yloxy)methyl]; 1,3-Propanediol, 2,2-bis[(2-propen-1-yloxy)methyl; and 1,3-Propanediol, 2-[(2,3-dibromopropoxy)methyl]-2-[(2-propen-1-yloxy)methyl]. Further compounds within the scope of formula (1) may be known to a person having ordinary skill in the art, and may be used in the present invention.

The weight ratio of over-indexed cross-linked thermoplastic polyurethane elastomer precursor to the unsaturated diols may generally be from about 100:0.1 to about 100:25. In particular embodiments, the weight ratio of cross-linked thermoplastic polyurethane elastomer precursor to the unsaturated diols may be about 100:10.

The inventors have discovered that a stoichiometric excess of isocyanate moieties of at least about 6 mol percent yields a product that resists shear failure yet remains a TPU elastomer, as does the precursor thereof. Thus, the over-indexed, optionally cross-linked TPU elastomer precursor described herein is particularly suitable for thermoforming, such as forming a cover on an article or an outer cover layer on a golf ball. The outer cover layer thus would resist stress failure that typically manifests itself as corrugations or 'hairs' on the surface of the golf ball, particularly if the thermoplastic polyurethane elastomer precursor is cross-linked. Thus, golf ball covers and other surfaces that require stress resistance, toughness, or hardness, such as livestock tags, shoe bindings, and furniture, also are suitably made with such material.

The index of over-indexed, optionally cross-linked TPU elastomer precursor in an embodiment herein is at least about 1.01, typically is at least about 1.06, typically is between about 1.06 and about 1.18, and still more typically between about 1.10 and about 1.15. In another embodiment, the index is between about 1.01 and about 1.35, typically between about 1.60 and about 1.35, more typically between about 1.06 and about 1.25, and even more typically between about 1.12 and about 1.18. A large excess of isocyanate, for example, an index greater than about 1.35, typically is a waste of reactant and leaves unreacted isocyanate, which is a source of unintended reactions that may form corrosive materials, even after the second curing step.

The skilled practitioner recognizes that large amounts of excess isocyanate, such as greater than about 5 percent excess, conventionally are avoided for a number of reasons. In addition to the fact that unreacted isocyanate may form corrosive materials, contact with isocyanate compound itself adversely affects some people. Further, isocyanate compounds are costly and are dense, thus adding weight to products and driving up costs without benefit to the process.

Optionally, the over-indexed, optionally cross-linked thermoplastic polyurethane elastomer precursor may include further components such as fillers and/or additives. These further compounds then appear in the thermoplastic polyurethane elastomer made from the precursor. Fillers and additives may be used based on any of a variety of desired characteristics, such as enhancement of physical properties, UV light resistance, and other properties. For example, to improve UV light resistance, the over-indexed cross-linked thermoplastic polyurethane elastomer may include at least one light stabilizer. Light stabilizers may include hindered amines, UV stabilizers, or a mixture thereof.

Inorganic or organic fillers can be also added to the over-indexed, optionally cross-linked thermoplastic polyurethane elastomer precursor. Suitable inorganic fillers may include silicate minerals, metal oxides, metal salts, clays, metal silicates, glass fibers, natural fibrous minerals, synthetic fibrous minerals, or a mixture thereof. Suitable organic fillers may include carbon black, fullerene and/or carbon nanotubes, melamine colophony, cellulose fibers, polyamide fibers, polyacrylonitrile fibers, polyurethane fibers, polyester fibers based on aromatic and/aliphatic dicarboxylic acid esters, carbon fibers or a mixture thereof. The inorganic and organic fillers may be used individually or as a mixture thereof. The total amount of the filler may be from about 0.5 to about 30 percent by weight of the polyurethane components.

Flame retardants may also be used to improve the flame resistance of the over-indexed cross-linked thermoplastic polyurethane elastomer. Suitable flame retardants may include organic phosphates, metal phosphates, metal polyphosphates, metal oxides (such as aluminum oxide hydrate, antimony trioxide, arsenic oxide), metal salts (such as calcium sulfate, expandable graphite), and cyanuric acid derivatives (such as melamine cyanurate). These flame retardants may be used individually or as a mixture thereof, and the total amount of the flame retardant may be from about 10 to about 35 percent by weight of the polyurethane components.

To improve toughness and compression rebound, the over-indexed, optionally cross-linked thermoplastic polyurethane elastomer may include at least one dispersant, such as a monomer or oligomer comprising unsaturated bonds. Examples of suitable monomers include styrene, acrylic esters; suitable oligomers include di- and tri-acrylates/methacrylates, ester acrylates/methacrylates, and urethane or urea acrylates/methacrylates. When a diacrylate-containing compound is used as a dispersant, it also may enter into the cross-linking reaction.

Over-indexed, optionally cross-linked thermoplastic polyurethane elastomer precursor used to form a visible part of an article may include at least one white pigment to aid in better visibility. The white pigment may be selected from the group consisting of titanium dioxide, zinc oxide, and a mixture thereof. Pigments of other colors may serve equally well, particularly in other articles, such as sports balls or livestock tags, for color-coding the articles, to increase visibility, or to increase the legibility of text printed thereon. With the guidance provided herein, the skilled practitioner can identify suitable additives.

In embodiments of the disclosure, the over-indexed, optionally cross-linked thermoplastic polyurethane elastomer may generally be formed by a single-screw, twin-screw, or a batch method in order to mix and react all of the ingredients described above. The products of the reaction process may be in the form of pellets or ground chips.

Figure 5:
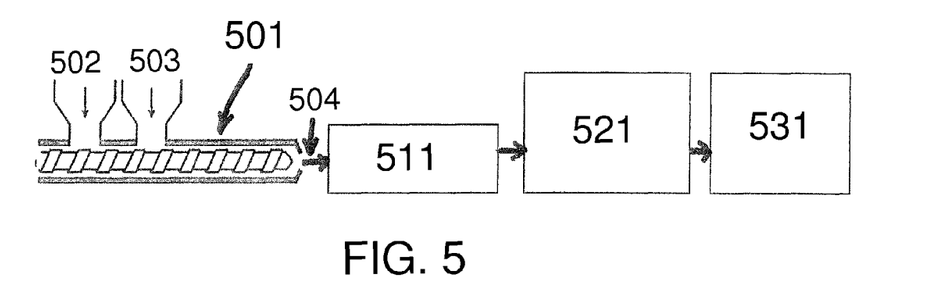
FIG. 5 illustrates a typical schematic flow diagram for the manufacture of thermoplastic polyurethane elastomer precursor.

FIG. 5 illustrates the manufacture of over-indexed, optionally cross-linked thermoplastic polyurethane elastomer precursor. This one-shot process is less complicated that processes that require formation of a pre-polymer, typically the reaction product of the isocyanate and the long-chain diol, then reacting the prepolymer with the remaining reactants, typically the chain extenders. Rather, as shown in FIG. 5, all reactants (502, 503) can be combined in a screw extruder (501) in a single process step. If the precursor or the thermoplastic polyurethane elastomer is to be cross-linked, free-radical initiator can be included at any step in the manufacturing and curing process. After the appropriate period of mixing, over-indexed, optionally cross-linked thermoplastic polyurethane elastomer precursor (504) having unreacted isocyanate moieties is extruded from the extruder.

If a single-screw or twin-screw process is used, the dwell times of the molten reaction mixture in the screw extruder may generally be in the range of from about 0.3 to about 10 minutes, and in some embodiments may be from about 0.4 to about 4 minutes. The temperature of the screw housing may be in the range of about 70° C. to 280° C. With the guidance provided herein, the skilled practitioner will be able to establish suitable reaction conditions.

The product of this reaction process is an over-indexed, optionally cross-linked thermoplastic polyurethane elastomer precursor having unreacted isocyanate moieties. In embodiments of the disclosure, the thermoplastic polyurethane elastomer precursor will be cross-linked if cross-linker and free-radical initiator were included in the extruder. In other embodiments of the disclosure, the cross-linker and free-radical initiator will be incorporated into the thermoplastic polyurethane elastomer precursor as part of the thermoplastic polyurethane elastomer formation before final reaction, i.e., when the precursor is shaped to form the article.

The precursor composition is sensitive to moisture, which will begin a reaction chain by reacting with the isocyanate moieties. Although the inventors do not wish to be bound by theory, it is believed that moisture reacts with the free isocyanate moieties to produce carbamic acid, which is relatively unstable and thus decomposes to form an amine and carbon dioxide. The amine then reacts with an isocyanate moiety to produce urea moieties, thus forming a thin shell of polyurethane/polyurea hybrid composition. The proportion of urethane and urea linkages will vary, depending on reaction concentrations. This thin shell may reduce reaction of additional isocyanate, but the shell does not completely preclude reaction.

In embodiments of the disclosure, extrudate 504 from extruder 501 typically is cooled and pelletized, or comminuted, in association with water bath 511. The water used in this cooling step typically reacts with some of the excess isocyanate. The inventors have discovered that drying the over-indexed material and protecting it from water until it is used to make thermoplastic polyurethane elastomer stops the consumption of isocyanate moieties and leaves excess isocyanate for secondary curing after the desired product, such as a shoe sole or a golf ball having the composition as an outer cover layer, is formed.

In embodiments of the disclosure, exposure of the precursor composition to water is limited by drying the precursor after water cooling. Thus, in embodiments of the disclosure, the moisture level in precursor is reduced to less than about 800 ppm water after water cooling.

Thus, in some embodiments of the method disclosed herein, the moisture concentration of precursor herein is reduced to less than about 3,000 ppm, typically less than about 2,000 ppm, more typically less than about 1,000 ppm, and even more typically less than about 800 ppm water immediately after water cooling. This moisture reduction may be carried out in any suitable manner. In some embodiments of the disclosure, the moisture is removed by heating.

In some embodiments of the disclosure, the precursor material may be dried and cured in an oven. In some embodiments of the disclosure, this oven drying is carried out after the first moisture reduction. In some embodiments of the disclosure, the oven drying is the only drying step. The moisture content is reduced to less than about 800 ppm, and more typically from about 300 ppm to about 500 ppm, by purging the oven with nitrogen or any inert gas. In some embodiments of the disclosure, the temperature in the oven is between about 70° C. and about 90° C., and typically about 80° C. In some embodiments of the disclosure, the heating period is between about 3 hours and 12 hours, and typically about 6 hours.

The inventors have discovered that packaging the material having less than about 800 ppm moisture in moisture-resistant containers, such as aluminum-lined bags/packages, ensures that the moisture content remains below about 800 ppm, typically below about 500 ppm, and more typically below about 300 ppm. In particular, maintenance of low water concentration ensures that sufficient excess isocyanate is available for the second curing of the product.

If a batch method is used to form the over-indexed, optionally cross-linked thermoplastic polyurethane elastomer precursor, all the components are molten and mixed together with a high agitated stir at a temperature in the range of about 70° C. to 120° C. for about 1 to about 3 minutes. Subsequently, the mixture is cured and pelletized, or comminuted, in a manner that keeps the moisture content as low as possible, and is stored in containers that maintain the moisture content below about 800 ppm. In embodiments of the disclosure, the moisture content of packaged precursor is less than about 800 ppm. In other embodiments of the disclosure, the moisture content of packaged precursor is between about 300 ppm and about 500 ppm.

The over-indexed, optionally cross-linked thermoplastic polyurethane elastomer precursor of the disclosure may be used to make articles, such as shoe soles, luggage tags, or golf balls, by injection molding or compression molding. Other articles can be made in the same way. Injection molding may be used in particular embodiments in order to achieve increased productivity. Generally, the free radical initiator may be added to the polymer mixture at any of several stages during manufacturing. For example, the free radical initiator may be added during extrusion of the polymer precursor, or during compression molding. Similarly, the free radical initiator may be activated so as to form cross-links during any of several stages of manufacturing. For example, the free radical initiator may be activated by heating during an extrusion process.

Typically, in embodiments of the disclosure, thermoplastic polyurethane elastomer precursor is comminuted, or pelletized, in association with water bath 511 to form pellets or granules. Often, these pellets retain a pellet shape, i.e., are roughly cylindrical. The inventors have discovered that pellets comprising thermoplastic polyurethane elastomer precursor having an NCO index greater than about 1.15 may not retain such a cylindrical shape when cooled. Rather, pellets having an NCO index greater than about 1.15 may form pillows or other flatter, less-defined shape because the thermoplastic polyurethane elastomer precursor is not as rigid as thermoplastic polyurethane elastomer precursor having an NCO index less than about 1.15. Thus, additional precautions or processing steps may be required to form rigid pellets, if this is deemed necessary. For example, if the resultant precursor pellets are soft, they may form indistinct shapes or may adhere to each other. Thus, it may become necessary to mechanically separate adhered precursor pellets, for example by striking the bag or container on a surface or prodding the pieces apart with a separator. Alternatively, it may be appropriate to form a harder thermoplastic polyurethane elastomer precursor. With the guidance provided herein, the skilled practitioner will be able to process softer pellets appropriately.

The thermoplastic polyurethane elastomer precursor compositions of this disclosure are subjected to a dual-curing process. The composition is chemically-cured when it is reacted with the diol chain extenders. Then, the resulting composition is moisture-cured in accordance with the steps described below.

The above-described chemical curing mechanism provides an over-indexed, optionally cross-linked thermoplastic polyurethane elastomer, which subsequently is fully-cured by contacting the composition with moisture. The resulting fully-cured composition has improved scuff resistance performance. Different methods may be used for applying the moisture to the composition in the moisture-curing step. For example, the partially-cured composition formed by the chemical-curing step simply may be exposed to ambient moisture for a sufficient period to fully-cure the material. Alternatively, a spray of moisture may be applied to the composition so that it fully cures. In another embodiment, a composition is soaked in hot water for one to two hours. In yet another embodiment, the composition is placed in a humidity chamber at relatively high humidity (particularly, the relative humidity is at least 50%.) In some embodiments of the disclosure, the humidity chamber has a temperature of 70° C., a relative humidity (RH) of 90%, and the composition is placed in the chamber for one to two hours to achieve good curing of the composition in a relatively short period.

Examples

Five thermoplastic polyurethane elastomer precursors were made, as follows:

TABLE 1

Thermoplastic Polyurethane Elastomer Precursors

| | F | G | H | I | J |
|---|---|---|---|---|---|
| PTMEG (pbw) | 100 | 100 | 100 | 100 | 100 |
| BG (pbw) | 15 | 15 | 15 | 15 | 15 |
| TMPME (weight % to total components) | 10% | 10% | 0 | 10% | 10% |
| DCP (weight % to total components) | 0.5% | 0.5% | 0 | 0 | 0 |

TABLE 1-continued

Thermoplastic Polyurethane Elastomer Precursors

| | F | G | H | I | J |
|---|---|---|---|---|---|
| MDI (pbw) | 92.1 | 102.6 | 55.0 | 92.1 | 102.6 |
| Molar ratio of organic isocyanate to oxy-hydrogen (hydroxyl) | 1.06:1.00 | 1.18:1.00 | 1.01:1.00 | 1.06:1.00 | 1.18:1.00 |

"PTMEG" is polytetramethylene ether glycol, having a number average molecular weight of 2,000, and is commercially available from Invista, under the trade name of Terathane® 2000. "BG" is 1,4-butanediol, commercially available from BASF and other suppliers. "TMPME" is trimethylolpropane monoallylether, commercially available from Perstorp Specialty Chemicals AB. "DCP" is dicumyl peroxide, commercially available from LaPorte Chemicals Ltd. "MDI" is diphenylmethane diisocyanate, commercially available from Huntsman, under the trade name of Suprasec® 1100.

Thermoplastic polyurethane elastomer precursor materials F, G, H, I and J were formed by mixing PTMEG, B G, TMPME, DCP, and MDI in the proportions shown. Specifically, these materials were prepared by mixing the components in a highly agitated stirrer for 1 minute, starting at a temperature of about 70° C., followed by a 10-hour post curing process at a temperature of about 100° C. Each post cured polyurethane elastomer precursor was ground into small chips. The manufacturing process maintained low moisture levels, including less than about 800 ppm after cooling and pelletizing, or comminution to form pellets, and less than about 300 ppm after secondary drying.

The thermoplastic polyurethane elastomer precursor materials of Table 1 were used, in combination with the materials described in Tables 2, 3, and 4 below, to manufacture five kinds of golf balls, as shown in Table 5.

For each golf ball, the inner core layer was made from a material selected from Table 2, the outer core layer was made from a material selected from Table 3, the inner cover layer was made from a material select from Table 4, and the cover layer was made from a material selected from Table 1. The amounts of the materials listed in Tables 2, 3, and 4 are shown in parts by weight (pbw) or percentages by weight.

TABLE 2

Inner Core Materials

| Resin: | A | B |
|---|---|---|
| HPF 2000* | 78 | 0 |
| HPF AD 1035* | 22 | 100 |

*HPF 2000 and HPF AD 1035 are trade names of ionomeric resins by E. I. DuPont de Nemours and Company

TABLE 3

Outer Core Material

| Rubber compound: | C | D |
|---|---|---|
| TAIPOL ™ BR0150* | 100 | 100 |
| Zinc diacrylate | 29 | 29 |
| Zinc oxide | 9 | 9 |
| Barium sulfate | 11 | 9 |
| Peroxide | 1 | 1 |

*TAIPOL ™ BR0150 is the trade name of a rubber produced by Taiwan Synthetic Rubber Corp.

TABLE 4

Inner Cover Material

| Resin: | E |
|---|---|
| Neothane 6303D* | 100 |

*Neothane 6303D is the trade name of a thermoplastic polyurethane produced by Dongsung Highchem Co. LTD.

Generally, the golf balls were manufactured using conventional compression molding and injection molding processes known in the art of golf ball manufacturing. After all golf balls were made, all golf balls were kept in an environment with a temperature of 30° C. and a relative humidity of 50 percent for 4 hours.

TABLE 5

Golf Ball Testing Data

| Ball Number | 1 | 2 | 3 | 4 | 5 |
|---|---|---|---|---|---|
| Inner Core Layer | | | | | |
| Material | A | B | A | B | A |
| Diameter (mm) | 24 | 21 | 24 | 21 | 24 |
| Shore D Hardness | 53 | 46 | 53 | 46 | 53 |
| Compression Deformation (mm) | 3.2 | 4.2 | 3.2 | 4.2 | 3.2 |
| COR | 0.83 | 0.81 | 0.83 | 0.81 | 0.83 |
| Outer Core Layer | | | | | |
| Material | C | D | C | D | C |
| Thickness (mm) | 7.25 | 8.75 | 7.25 | 8.75 | 7.25 |
| Shore D Hardness | 59 | 58 | 59 | 58 | 59 |
| Inner Cover Layer | | | | | |
| Material | E | E | E | E | E |
| Thickness (mm) | 1.0 | 1.0 | 1.0 | 1.0 | 1.0 |

TABLE 5-continued

Golf Ball Testing Data

| Ball Number | 1 | 2 | 3 | 4 | 5 |
|---|---|---|---|---|---|
| Shore D Hardness | 69 | 68 | 69 | 68 | 69 |
| Flexural Modulus (psi) | 77,000 | 77,000 | 77,000 | 77,000 | 77,000 |
| Outer cover layer | | | | | |
| Resin | F | G | H | I | J |
| Thickness (mm) | 1.1 | 1.1 | 1.1 | 1.1 | 1.1 |
| Shore D Hardness | 53 | 52 | 53 | 52 | 53 |
| Flexural Modulus(psi) | 550 | 530 | 480 | 490 | 490 |
| Ball | | | | | |
| COR | 0.785 | 0.775 | 0.785 | 0.775 | 0.785 |
| Scuff Resistance | | | | | |
| Rating | 2.5 | 1.5 | 4 | 3.5 | 3 |

A scuff resistance test was conducted in the following manner: a Nike Victory Red forged standard sand wedge (loft: 54'; bounce: 12'; shaft: True Temper Dynamic Gold shaft; flex: S) is fixed to a swing robot manufactured by Miyamae Co., Ltd. and then swung at the head speed of about 32 m/s. The club face was oriented for a square hit. The forward/backward tee position was adjusted so that the tee was four inches behind the point in the downswing where the club was vertical. The height of the tee and the toe-heel position of the club relative to the tee were adjusted in order that the center of the impact mark was about ¾ of an inch above the sole and was centered toe to heel across the face. Three samples of each ball were tested. Each ball was hit three times.

Other methods may also be used to determine the scuff resistance, such as the methods described in the commonly assigned copending application titled "Golf Ball Wear Indicator", U.S. application Ser. No. 12/691,282, filed Jan. 21, 2010, in the name of Brad Tutmark.

After the above described scuff resistance testing, each golf ball cover was visually observed and rated according to the following scale: a golf ball cover was rated "1" when little or no damage was visible, only groove markings or dents; a golf ball cover was rated "2" when small cuts and/or ripples in the cover were apparent; a golf ball cover was rated "3" when moderate amounts of cover material were lifted from the ball's surface, but the cover material was still attached to the ball; and finally a golf ball cover was rated "4" when cover material was removed or barely attached to the golf ball.

Shore D hardness values of the core and cover layer were measured on the spherical surface of the layer to be measured by using a Shore D hardness tester.

As shown in Table 5, golf balls 1 and 2 made from compositions including an over-indexed, cross-linked thermoplastic polyurethane elastomer having cross-links located in the hard segments, where the cross-links are the reaction product of unsaturated bonds located in the hard segments as catalyzed by a free radical initiator and a proper ratio of the organic isocyanate to the long chain polyol, provides superior scuff resistance. The other three balls, although not as scuff-resistant, clearly indicate that increasing NCO index increased scuff resistance. Although golf balls 3-5 do not exhibit the scuff resistance of golf balls 1 and 2, the thermoplastic polyurethane elastomer has desirable properties and characteristics for the manufacture of other articles requiring, for example, good Shore D hardness and flexural modulus.

The same thermoplastic polyurethane elastomer precursors were used with the same outer core materials and inner cover material other inner core materials, golf balls were made in accordance with the exemplified method, with inner core material selected from Table 6, outer core material from Table 3, inner cover material from Table 4, and outer cover material from Table 1.

TABLE 6

| Inner Core Materials | |
|---|---|
| Resin: | M |
| HPF 2000* | 45 |
| HPF AD 1035* | 35 |
| Masterbatch ** | 20 |

*HPF 2000 and HPF AD 1035 are trade names of ionomeric resins by E. I. DuPont de Nemours and Company.
** Masterbatch comprises 40 parts by weight of Surlyn ® 8940 and 60 parts by weight of barium sulfate.

TABLE 7

Golf Ball Testing Data

| Golf ball number | 6 | 7 | 8 | 9 | 10 |
|---|---|---|---|---|---|
| Inner Core Layer | | | | | |
| Material | M | M | M | M | M |
| Diameter (mm) | 24 | 21 | 24 | 21 | 24 |
| Shore D Hardness | 53 | 53 | 53 | 53 | 53 |
| Compression Deformation (mm) | 3.5 | 3.5 | 3.5 | 3.5 | 3.5 |
| COR | 0.799 | 0.799 | 0.799 | 0.799 | 0.799 |

TABLE 7-continued

Golf Ball Testing Data

| Golf ball number | 6 | 7 | 8 | 9 | 10 |
|---|---|---|---|---|---|
| Outer Core Layer | | | | | |
| Material | C | C | C | C | C |
| Thickness (mm) | 7.25 | 8.75 | 7.25 | 8.75 | 7.25 |
| Shore D Hardness | 59 | 59 | 59 | 59 | 59 |
| Inner Cover Layer | | | | | |
| Material | E | E | E | E | E |
| Thickness (mm) | 1.0 | 1.0 | 1.0 | 1.0 | 1.0 |
| Shore D Hardness | 69 | 68 | 69 | 68 | 69 |
| Flexural Modulus (psi) | 77,000 | 77,000 | 77,000 | 77,000 | 77,000 |
| Outer cover layer | | | | | |
| Resin | F | G | H | I | J |
| Thickness (mm) | 1.1 | 1.1 | 1.1 | 1.1 | 1.1 |
| Shore D Hardness | 54 | 54 | 53 | 53 | 53 |
| Flexural Modulus(psi) | 520 | 540 | 480 | 490 | 490 |
| 100% Modulus (kg/cm$^2$) | 120 | 125 | 105 | 110 | 110 |
| Ball | | | | | |
| COR | 0.785 | 0.785 | 0.784 | 0.785 | 0.785 |
| Scuff Resistance | | | | | |
| Rating | 2.0 | 1.5 | 4 | 3.5 | 3 |

As shown in Table 7, the golf balls made from compositions including an over-indexed cross-linked thermoplastic polyurethane elastomer having cross-links located in the hard segments, where the cross-links are the reaction product of unsaturated bonds located in the hard segments as catalyzed by a free radical initiator and a proper ratio of the organic isocyanate to the long chain polyol, provides superior scuff resistance. Golf balls 1 and 2 exhibit the same scuff-resistance as golf balls 6 and 7. Similarly, golf balls 3-5 and 8-10 exemplify the increased scuff resistance of material with increasing NCO index.

While various embodiments of the invention have been described, the description is intended to be exemplary, rather than limiting and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims. For example, different precursor compositions, perhaps those having a different isocyanate or polyol, also fall within the scope of the claims.

We claim:

1. A method for making a dried over-indexed thermoplastic polyurethane elastomer precursor having unreacted isocyanate moieties, the method comprising:
   combining reactants and reacting them to form an over-indexed thermoplastic polyurethane elastomer precursor,
   cooling the over-indexed thermoplastic polyurethane elastomer precursor in water to form cooled precursor,
   pelletizing the cooled precursor to form cooled precursor pellets,
   drying the cooled precursor pellets to a moisture concentration less than about 800 ppm to form dried over-indexed thermoplastic polyurethane elastomer precursor, and
   packaging the dried over-indexed thermoplastic polyurethane elastomer precursor in moisture-resistant packaging under conditions that essentially maintain the moisture content of the dried over-indexed thermoplastic polyurethane elastomer precursor at or below about 800 ppm.

2. The method of claim 1, wherein the drying further comprises
   partially drying the cooled precursor pellets to a moisture concentration less than about 3,000 ppm by heating to form partially dried precursor pellets and
   further drying the partially dried precursor pellets to a moisture concentration less than about 800 ppm in an inert gas flow to form dried over-indexed thermoplastic polyurethane elastomer precursor.

3. The method of claim 1, wherein the cooled precursor pellets are partially dried to a moisture concentration less than about 1,000 ppm.

4. The method of claim 2, wherein the cooled precursor pellets are partially dried to a moisture concentration less than about 1,000 ppm.

5. The method of claim 1, wherein the dried over-indexed thermoplastic polyurethane elastomer precursor has a moisture content of 500 ppm.

6. The method of claim 5, wherein the dried over-indexed thermoplastic polyurethane elastomer precursor has a moisture content of 300 ppm.

7. The method of claim 2, wherein the dried over-indexed thermoplastic polyurethane elastomer precursor has a moisture content of 300 ppm.

8. The method of claim 2, wherein the partially dried precursor pellets are further dried at a temperature between about 70° C. and about 90° C. with inert gas flow.

9. The method of claim 5, wherein the partially dried precursor pellets are further dried at a temperature between about 70° C. and about 90° C. with inert gas flow.

10. The method of claim 1, wherein the over-indexed thermoplastic polyurethane elastomer precursor comprises a cross-linking agent.

11. The method of claim 1, wherein the dried over-indexed thermoplastic polyurethane elastomer precursor has an NCO index of between about 1.05 and about 1.35.

12. The method of claim 11, wherein the dried over-indexed thermoplastic polyurethane elastomer precursor has an NCO index of between about 1.06 and about 1.18.

13. A method for making over-indexed thermoplastic polyurethane elastomer, said method comprising:
    making an over-indexed thermoplastic polyurethane elastomer precursor having unreacted isocyanate moieties by combining reactants and reacting them to form an over-indexed thermoplastic polyurethane elastomer precursor,
    cooling the over-indexed thermoplastic polyurethane elastomer precursor in water to form cooled precursor,
    pelletizing the cooled precursor to form cooled precursor pellets,
    drying the cooled precursor pellets to a moisture concentration less than about 800 ppm to form dried over-indexed thermoplastic polyurethane elastomer precursor,
    packaging the dried over-indexed thermoplastic polyurethane elastomer precursor in moisture-resistant packaging under conditions that essentially maintain the moisture content of the dried over-indexed thermoplastic polyurethane elastomer precursor at or below about 800 ppm; and
    removing the dried over-indexed thermoplastic polyurethane elastomer precursor from the package and curing the dried over-indexed thermoplastic polyurethane elastomer precursor by contact with water.

14. The method of claim 13, wherein the drying further comprises
    partially drying the cooled precursor pellets to a moisture concentration less than about 3,000 ppm by heating to form partially dried precursor pellets and
    further drying the partially dried precursor pellets to a moisture concentration less than about 800 ppm in an inert gas flow to form dried over-indexed thermoplastic polyurethane elastomer precursor.

15. The method of claim 13, wherein the cooled precursor pellets are partially dried to a moisture concentration less than about 1,000 ppm.

16. The method of claim 14, wherein the cooled precursor pellets are partially dried to a moisture concentration less than about 800 ppm.

17. The method of claim 13, wherein the dried over-indexed thermoplastic polyurethane elastomer precursor has a moisture content of 500 ppm.

18. The method of claim 17, wherein the dried over-indexed thermoplastic polyurethane elastomer precursor has a moisture content of 300 ppm.

19. The method of claim 14, wherein the dried over-indexed thermoplastic polyurethane elastomer precursor has a moisture content of 300 ppm.

20. The method of claim 15, wherein the packaged pelletized precursor material has a moisture content of 300 ppm.

21. The method of claim 15, wherein the partially dried precursor pellets are further dried at a temperature between about 70° C. and about 90° C. with inert gas flow.

22. The method of claim 14, wherein the partially dried precursor pellets are further dried at a temperature between about 70° C. and about 90° C. with inert gas flow.

23. The method of claim 13, wherein the over-indexed thermoplastic polyurethane elastomer precursor comprises a cross-linking agent.

24. The method of claim 13, wherein the dried over-indexed thermoplastic polyurethane elastomer precursor has an NCO index of between about 1.05 and about 1.35.

25. The method of claim 24, wherein the dried over-indexed thermoplastic polyurethane elastomer precursor has an NCO index of between about 1.06 and about 1.18.

26. A method for making an article comprising over-indexed thermoplastic polyurethane elastomer, said method comprising:
    making an over-indexed thermoplastic polyurethane elastomer precursor having unreacted isocyanate moieties by combining reactants and reacting them to form an over-indexed thermoplastic polyurethane elastomer precursor,
    cooling precursor in water and pelletizing cooled precursor to form precursor pellets,
    drying the precursor pellets to a moisture concentration less than about 800 ppm to form dried precursor pellets,
    processing the dried precursor pellets to form an article precursor, and curing the article precursor by contact with water to form the article.

27. The method of claim 26, wherein the cooled, pelletized precursor is dried to a moisture concentration less than about 500 ppm.

28. The method of claim 26, further comprising
    packaging the dried precursor pellets in moisture-resistant packaging under conditions that essentially maintain the moisture content of the dried precursor pellets at or below about 800 ppm, and
    removing the dried precursor pellets from the package before processing the dried precursor pellets to form an article precursor.

29. The method of claim 26, wherein the packaged pelletized precursor material has a moisture content of 500 ppm.

30. The method of claim 26, wherein the dried precursor pellets have an NCO index of between about 1.05 and about 1.35.

31. The method of claim 30, wherein the dried precursor pellets have an NCO index of between about 1.06 and about 1.18.

* * * * *